United States Patent [19]

Lieberman et al.

[11] Patent Number: 4,906,450
[45] Date of Patent: Mar. 6, 1990

[54] TREATMENT OF ARTHRITIS, INCLUDING RHEUMATOID ARTHRITIS, WITH THE RADIONUCLIDE, TIN SN-121

[76] Inventors: Ephraim Lieberman, 1 Victory Rd., Suffern, N.Y. 10901; Maurice E. Bordoni, R.D. 1, Box 680, Westtown, N.Y. 10998; Alfred K. Thornton, Box 500 Lower Rd., New Hampton, N.Y. 10958

[21] Appl. No.: 30,388

[22] Filed: Mar. 26, 1987

[51] Int. Cl.$^4$ .......................... A61K 43/00; A61N 5/12
[52] U.S. Cl. ...................................... 424/1.1; 424/633; 424/639; 424/647; 424/653; 424/655; 424/689; 600/3
[58] Field of Search ................. 424/1.1, 131; 423/249; 514/825; 128/1.1; 600/3

[56] References Cited

U.S. PATENT DOCUMENTS 4,511,551 4/1985 Cardarelli et al. .................... 424/1.1
4,533,541 8/1985 Srivastava et al. .................... 424/1.1

OTHER PUBLICATIONS

Erdar et al. "J. Inorg. Nucl. Chem.", 1968, 30(8) pp. 1985–1993 [Chemical Abstracts vol. 68, 1968.]
Sledge et al, "Expermental Radiation", Arthritis and Rheumatism, vol. 20, No. 7, Sep.–Oct. 1977, 1334–1342.

*Primary Examiner*—John S. Maples
*Attorney, Agent, or Firm*—Leonard Bloom

[57] ABSTRACT

The radionuclide Tin, Sn-121 in a carrier hydroxide aggregate is disclosed for the treatment of arthritis and, in particular, rheumatoid arthritis of the hands, the interphalangeal joints of the fingers and the metacarpal joints of the hand.

The radioactive compound disclosed preferably has a particle size of <90 microns. The beta energy emission associated with Tin, Sn-121 has an energy of 0.38 meV. There are no gamma photons emited during the decay of Tin, Sn-121 to stable Antimony Sb-121. The half life of Tin, Sn-121 is 27.06 hours.

The method of preparation of the compound is disclosed along with the method of administration to the patient in need thereof.

37 Claims, No Drawings

TREATMENT OF ARTHRITIS, INCLUDING RHEUMATOID ARTHRITIS, WITH THE RADIONUCLIDE, TIN SN-121

FIELD OF THE INVENTION

The present invention relates to the use of a compound, radioactive Tin, Sn-121, for treating arthritis, in particular rheumatoid arthritis of the fingers (interphalangeal joints and the metacarpal joints of the hand).

Methods for the preparation of the compound are described.

BACKGROUND OF THE INVENTION

Arthritic disorders are the second leading cause of losses in time and earnings in the United States. Approximately six million (6,000,000) people are afflicted with rheumatoid arthritis. Of these, over eighty percent (80%) ultimately will have involvement of the hand joint, over fifty percent (50%) will involve the knee joint, and somewhat smaller percentages will have involvement of other joints such as the ankle, elbow, and shoulder. Rheumatoid arthritis is believed to be an autoimmune disease wherein parts of the body are attacked by antibodies manufactured in the body. These antibodies may be produced in response to viruses present in the body. While the mechanism for rheumatoid arthritis is not known, it is a systemic disease. When the disease is active, the erythrocyte sedimentation rate (ESR) is usually elevated and the blood tests usually positive for rheumatoid factor.

A source of disability for the sufferer of rheumatoid arthritis is an inflammatory response, of unknown origin, in the synovium, or lining, of the afflicted joint. This chronic inflammation, or synovitis, leads to pannus formation and eventually, destruction of the joint cartilage.

Presently, the primary method of treating rheumatoid arthritis is by use of compounds directed at blocking the inflammatory process. These compounds include aspirin, penicillamine, gold salts, and many other ethical drugs. Unfortunately these attempts are often unsuccessful and the relief provided is temporary at best. In the knee, a primary alternative is the surgical excision of the inflamed synovium in a procedure known as surgical synovectomy. In this procedure, the abnormal synovium and pannus formation are surgically removed. While in many cases this procedure proves to arrest the disease, it also has a significant number of drawbacks and limitations. Among these are limitations on complete removal of the inflamed synovium, the risks and dangers inherent in the operation itself; and the required lengthy recovery period, much of which is spent in the hospital.

However, surgical procedures to treat rheumatoid synovitis of the phalangeal joints or of the metacarpophalangeal joints is not satisfactorily done. Thus the development of a suitable agent for treating rheumatoid synovitis of these interphalangeal or metacarpo-phalangeal joints is of significance. This is the basis for utilizing Tin, Sn-121.

In order to overcome these problems, attempts have been made to destroy the diseased synovium by the performance of a procedure known as radiation synovectomy. Intra-articular injection of colloidal gold-198 ($^{198}$Au) has bsen reported to abate inflamed synovium (Fellinger et al, 33 WEIN Z. INN, Med. 351, (1952) and Ansell et al, 22 Ann. Rheum. Dis. 435 (1963). Unfortunately this procedure is disadvantageous due to the small particle size of the gold colloid utilized and the high energy gamma emitted during decay (gamma emission). This emission poses dangers to the patient by increasing the whole body dose, thereby exposing healthy tissue to radiation, and posing substantial difficulties with radiation protection for hospital personnel.

The use of other radionuclides has also been attempted in radiation synovectomy. These radionuclides include Erbium-169 ($^{169}$Er) as reported in Menkes et al, 36 Ann. Rheum. Dis. 254 (1977); Rhenium-186 ($^{186}$Re) as reported in Deckart et al, 3 Radiobiol, Radiother 363 (1979) and in DelBarre et al, 2 Nouv. Presse. Med 1372 (1973); Phosphorus-32 ($^{32}$P) as reported in Wenston et al, 14 J. Nuc. Med 886 (1973), and Yttrium-90 (90Y) as reported in Gumpel et al, 48 Br. J. Radiol. 377 (1975).

Each of these radionuclides ($^{169}$Er, $^{186}$Re, $^{32}$P, $^{198}$Au, and $^{90}$Y) has proven disadvantageous due to either the long physical half-life of the particular radionuclide involved, the small particle size of the system, and/or the occurrence of significant amounts of radioactivity leaking from the affected joints and associated chromosomal aberrations in the lymphocytes of the patient. (See also; Oka et al, 17 Acta Rheum. Scand. 148 (1971) and Virkkunen et al, 13 Acta Rheum., Scand., (1967).

Currently the preferred radionuclide for the interphalangeal or metacarpo-phalangeal joints is $^{169}$Er in various forms. Its disadvantages however include an excessively long physical half-life of 9.4 days. Many physicians would not utilize a preparation with such a long half-life in treating rheumatoid synovitis.

Because the synovial space associated with the proximal interphalangeal or metacarpo-phalangeal joints, the emission energy of the radionuclide must be significantly lower than the agents that would be utilized to treat the larger knee joint. Hence $^{90}$Y, $^{198}$Au, $^{165}$Dy, or $^{166}$Ho are not attractive agents in this application involving interphalangeal or metacarpo-phalangeal joints. Tin, Sn-121 possesses excellent nuclear properties for treating these joints. The properties include half-life of 27 hours, low energy beta emission, and no gamma photons. In addition, the chemistry of Tin, (Sn) is well known and is useful in the preparation of the compound incorporating Tin, Sn-121.

SUMMARY OF THE INVENTION

According to this invention, certain radioactive compounds have utility in radiation synovectomy for the treatment of rheumatoid arthritis. In accordance with the teachings of this invention, desired factors include: safety, effectiveness, a relatively large particulate carrier, beta emissions of a desired energy and half-life that permits distribution and not high levels of other types of energies which can damage healthy tissue. Also, in accordance with this invention, other desirable physical properties include a radionuclide having a half-life which is both long enough to permit the compound's central preparation and distribution and short enough to reduce the effects of potential leakage.

We have found that compounds having a Tin, Sn-121 radionuclide exhibit the aforementioned physical properties.

Accordingly, it is the primary object of this invention to provide a radioactive isotope in a form useful in the treatment of arthritis, and more particularly, useful for radiation synovectomy in the treatment of rheumatoid arthritis, especially rheumatoid arthritis of the interphalangeal or metacarpo-phalangeal joints.

It is still another object to provide a radioactive compound for the treatment of arthritis, and more particularly, rheumatoid arthritis which can be prepared at, and distributed from, a central location utilizing existing transportation channels.

It is yet still another object of this invention to provide methods for the preparation of a radioactive compound useful in radiation synovectomy for the treatment of rheumatoid arthritis.

It is another object of this invention to provide methods for the treatment of arthritis and, more particularly, rheumatoid arthritis.

These and other objects are accomplished by one or more embodiments made in accordance with the teachings of the present invention.

In accordance with the teachings of the present invention, Tin, Sn-121 isotope is provided in a form useful for the treatment of arthritis, and more particularly in a form which is useful for radiation synovectomy in the treatment of rheumatoid arthritis.

In further accordance with the teachings of the present invention, a radioactive compound including Tin, Sn-121 is provided for the treatment of arthritis, and more particularly rheumatoid arthritis, which can be prepared at and distributed from a central location utilizing existing channels of transportation.

In still further accordance with the teachings of the present invention methods for the preparation of radioactive compounds useful in radiation synovectomy for the treatment of rheumatoid arthritis.

In still yet further accordance with the teachings of the present invention, there is provided a method for the treatment of arthritis and, more particularly, rheumatoid arthritis.

The nature and substance of the present invention, as well as its objectives and advantages, will be more clearly perceived and fully understood by reference to the following description and claims.

DESCRIPTION OF PREFERRED EMBODIMENTS

The radioactive compound of the present invention has particular utility in the treatment of arthritis and, more specifically, in the treatment of rheumatoid arthritis. It also had particular utility for use in radiation synovectomy.

The radioactive specie of the present invention is Tin, Sn-121 nuclide. Tin, Sn-121 has a half-life of 27.06 hours which allows for sufficient time following production of the isotope in a nuclear reactor for the preparation and distribution of the finished compound using existing transportation channels. Tin, Sn-121 has a principal beta energy of 0.38 meV. It is this energy which makes the Tin, Sn-121 radionuclide particularly useful as a radiation synovectomy agent for small joints such as interphalangeal or metacarpo-phalangeal.

Tin, Sn-121 decays by beta emission to non-radioactive stable Antimony, Sb-121. There are no contaminating gamma photons associated with the decay of Tin, Sn-121.

Tin, Sn-121 is prepared by irradiating Tin, Sn-120 in a nuclear reactor. The Tin, Sn-120 captures neutrons to become radioactive Tin, Sn-121. The starting material for irradiation in a nuclear reactor can be a naturally occurring Tin (Sn) metal or oxide form or an isotopically enriched Tin, Sn-120, metal or oxide form. It is not essential that enriched targets be used.

Tin, Sn-121 has an average soft tissue penetration of approximately 0.5 mm with a maximum soft tissue penetration of approximately 1 mm.

The preferred chemical form of Tin, Sn-121 is that of the Hydroxide. However, it is to be understood that the Tin, Sn-121 radionuclide is useful in a variety of suitable particle configurations.

The preferred radioactive chemical compound of the present invention is Tin, Sn-121 Hydroxide in a carrier of ferric hydroxide macroaggregate (FHMA). It is to be noted that other compounds such as Tin Hydroxide in a carrier aluminum hydroxide macroaggregate (AHMA) or Tin Hydroxide formed in the presence of other soluble transition metal chlorides (i.e. Bismuth and Chromium, to name but two), would also suffice. In that particle size of the radioactive compound has a major impact on the leakage rate, the preferred radioactive compound has a minimum particle size of 1 micron. As practiced and prepared herein, the Tin, Sn-121 ferric hydroxide aggregate carrier has an overall particle size range from 1 micron to 90 microns, with >90% of all particles falling within the range of 5 to 30 microns.

While not required, it is preferred that the aggregate is in a suspension which further contains a stabilizing ingredient to aid in preventing further aggregation of the particles in the preparation. This stabilizing agent includes high molecular weight polymers such as polyvinyl pyrrolidone (PVP). Other high molecular weight polymers such as polyoxypropylene-polyoxyethylene block-copolymer may be combined with the macroaggregate suspension to afford the same protective action.

METHOD OF PREPARATION

The radioactive compound is prepared by the following method: the irradiation of the target material, Tin, natural occurring or isotopically enriched in Tin, Sn-120, is known to those skilled in the art. The chemical form of the target material can be metallic Tin (Sn), or stannous oxide (SnO).

The nuclear production process is as follows:

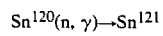

$(n, \gamma)$ = neutron in, gamma out

The target material is subjected to bombardment by neutrons in a nuclear reactor at a suitable thermal flux producing the desired radioactive specie element Tin, Sn-121.

At the end of the irradiation cycle, the target material is removed from its irradiation capsule and transferred to a dissolution vessel. The target material is subsequently converted to the Chloride form by the action of concentrated Hydrochloric Acid (35–38% acid). The target material Tin (Sn) is converted to Stannous Chloride, $SnCl_2$, the Stannous Oxide (SnO) is converted to Stannous Chloride, $SnCl_2$.

The preferred chemical form for radiation synovectomy is performed by the following basic chemical reaction:

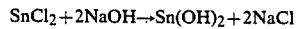

The ferric hydroxide macroaggregate is performed by the following basic chemical reaction:

$$SnCl_2 + FeCl_3 + 5NaOH \rightarrow Sn(OH)_2 + Fe(OH)_3 + 5NaCl$$

The preferred method of preparation is the following: 1 gm of irradiated Tin Wire (Sn metal) is dissolved in 5 mL of 12N Hydrochloric Acid. Slight applied heat may be needed to complete the dissolution of the Tin Wire.

After complete dissolution the Stannous Chloride solution is transferred quantatatively to a 25 mL volumetric flask and brought up to volume with 6N Hydrochloric Acid. A sample aliquot is removed for radiometric assay to determine the Sn-121 concentration in millicuries/milliliters.

A suitable aliquot containing ~10 millicuries of Sn-121 is asceptically transferred through a 0.2 micron filter into a 5 mL serum finish vial. The vial contains a 0.5 mL solution of 250 micrograms of Fe as $FeCl_3$ and 5 milligrams of Povidone all in 0.5N Hydrochloric Acid, all sterile and pyrogen free.

Depending on the volume of the radioactive (Sn-121) chloride solution a small volume of 3N NaOH solution is asceptically transferred through a 0.2 micron filter into the serum vial. The vial is mixed by inversion and placed in a boiling water bath ~100° C. for 5 minutes. The drug preparation is ready for use.

EXAMPLE

| | |
|---|---|
| 0.5 mL Sn-121 Solution = | 3.6 milliequivalents of $H^+$ ion |
| 0.5 mL Fe/Povidone Solution = | 0.25 milliequivalents of $H^+$ ion |
| | Total 3.85 milliequivalents of $H^+$ ion |
| 1.28 mL of NaOH Solution | |
| 1.28 × 3N = 3.84 | |
| meq. of $OH^+$ ion | |

The final solution should fall within the pH range of 6-7 pH.

The Stannous (Sn-121) Hydroxide ferric macroaggregate suspension can be suitably packaged and shipped to its ultimate point of use by existing transportation channels.

Administration of the radioactive drug is performed by methods well known to those skilled in the art. By way of example, the preferred method of administration to the fingers of an individual is by intra-articular injection. This administration is exemplified by the following example:

EXAMPLE I

The injection will be performed in the patient's room or in any other suitable location with monitoring by hospital personnel. Patient will be in the supine or sitting position.

The hand will be washed with, preferably, a betadine solution. One percent lidocaine hydrochloride will be instilled in the skin and subcutaneous tissue.

A 3-way stopcock/needle assembly will be utilized for drug administration. A 26 gauge needle will be employed. The aggregate suspension of Tin, Sn-121 will be injected into the joint space using the technique well known to those skilled in the art. The needle and needle tract are to be cleansed by flushing with 1% lidocaine hydrochloride through the 3-way stopcock assembly as the needle is withdrawn.

It will be understood by those skilled in the art that the exact amount of radioactive compound to administer as a therapeutic agent is also within the skill of the practitioner. However, by way of example, if the practitioner desires to deliver a dose of 5,000 rads to an afflicted finger, he must merely use classic techniques, well known to those skilled in the art. Assume a homogenous distribution of radioactivity in the finger joint without extra-articular leakage in order to arrive at quantity of radioactive compound to administer. We have found that 4 mCi Tin, Sn-121 FHMA will deliver approximately 5,000 rad dose to the diseased fingers.

What is claimed is:

1. A radioactive suspension for treatment of arthritis including a $^{121}$Tin compound in aggregation with ferric hydroxide.

2. A radioactive suspension for treatment of arthritis including a $^{121}$Tin compound in aggregation with aluminum hydroxide.

3. A radioactive suspension for treatment of arthritis wherein said suspension includes a 121Tin compound in aggregation with a metallic hydroxide.

4. The radioactive suspension of claim 3, wherein the suspension is a macroaggregate.

5. The suspension of claim 4, wherein the aggregation includes a metallic hydroxide macroaggregate.

6. A radioactive suspension for treatment of arthritis including a $^{121}$Tin compound in aggregation with a metal hydroxide selected from the group consisting of Bismuth Hydroxide, Chromium Hydroxide, Cupric Hydroxide, and Manganese Hydroxide.

7. A radioactive suspension for treatment of arthritis including a $^{121}$Tin compound in aggregation with a ferric hydroxide macroaggregate.

8. A radioactive suspension for treatment of arthritis including a $^{121}$Tin compound in aggregation with an aluminum hydroxide macroaggregate.

9. A radioactive suspension for treatment of arthritis including $^{121}$Tin in aggregation with a metal hydroxide, wherein the suspension includes a macroaggregate of a metal hydroxide selected from the group consisting of Bismuth Hydroxide, Chromium Hydroxide, Cupric Hydroxide and Manganese Hydroxide.

10. A radioactive compound for the treatment of arthritis comprising $^{121}$Tin Hydroxide and further including a ferric hydroxide aggregate.

11. A radioactive compound for the treatment of rheumatoid arthritis comprising $^{121}$Tin Hydroxide and further including a ferric hydroxide aggregate.

12. A radioactive compound for the treatment of rheumatoid arthritis comprising $^{121}$Tin Hydroxide and further including a ferric hydroxide macroaggregate.

13. A radioactive compound for the treatment of rheumatoid arthritis comprising $^{121}$Tin Hydroxide and further including an aluminum hydroxide aggregate.

14. A radioactive compound for the treatment of rheumatoid arthritis comprising $^{121}$Tin Hydroxide and further including an aluminum hydroxide macroaggregate.

15. A radioactive compound for the treatment of rheumatoid arthritis comprising $^{121}$Tin Hydroxide and further including a metallic hydroxide aggregate.

16. The compound of claim 15, wherein the metallic hydroxide aggregate is a transition metallic hydroxide selected from the group consisting of Bismuth Hydroxide, Chromium Hydroxide, Cupric Hydroxide and Manganese Hydroxide.

17. A radioactive compound for the treatment of rheumatoid arthritis comprising $^{121}$Tin Hydroxide and further including a metallic hydroxide macroaggregate.

18. The compound of claim 17, wherein the metallic hydroxide macroaggregate is a transition metallic hydroxide selected from the group consisting of Bismuth Hydroxide, Chromium Hydroxide, Cupric Hydroxide and Manganese Hydroxide.

19. A radioactive compound for the treatment of arthritis comprising $^{121}$Tin in a metallic hydroxide aggregate carrier having a particle size of approximately from 1 micron-90 microns, Beta energy emissions of said $^{121}$Tin being substantially 0.38 MeV, and a half-life of approximately 27.06 hours.

20. A method for the treatment of arthritis of an articular joint comprising: administering by injection a therapeutically effective quantity of a suspension including $^{121}$Tin to perform radiation synovectomy.

21. A radioactive composition for the treatment of arthritis comprising a compound which includes $^{121}$Tin and an aggregated metal hydroxide.

22. The radioactive composition of claim 21, wherein the aggregated metal hydroxide is a macroaggregate.

23. A radioactive composition for the treatment of arthritis comprising a compound which includes $^{121}$Tin and an aggregated metal hydroxide wherein the metal hydroxide is ferric hydroxide.

24. A radioactive composition for the treatment of arthritis comprising a compound which includes $^{121}$Tin and an aggregated metal hydroxide wherein the metal hydroxide is an aluminum hydroxide.

25. A radioactive composition for the treatment of arthritis comprising a compound which includes $^{121}$Tin and an aggregated metal hydroxide wherein the metal hydroxide is selected from the group consisting of Bismuth Hydroxide, Chromium Hydroxide, Cupric Hydroxide, and Manganese Hydroxide.

26. A radioactive composition for the treatment of arthritis comprising a compound which includes $^{121}$Tin and an aggregated metal hydroxide wherein the aggregated metal hydroxide is a macroaggregate, and wherein the metal hydroxide is ferric hydroxide.

27. A radioactive composition for the treatment of arthritis comprising a compound which includes $^{121}$Tin and an aggregated metal hydroxide wherein the aggregated metal hydroxide is a macroaggregate, and wherein the metal hydroxide is an aluminum hydroxide.

28. A radioactive composition for the treatment of arthritis comprising a compound which includes $^{121}$Tin and an aggregated metal hydroxide wherein the aggregated metal hydroxide is a macroaggregate, and wherein the metal hydroxide is selected from the group consisting of Bismuth Hydroxide, Chromium Hydroxide, Cupric Hydroxide, and Manganese Hydroxide.

29. A radioactive composition for the treatment of arthritis comprising $^{121}$Tin Hydroxide with a carrier of ferric hydroxide aggregate.

30. A radioactive composition for the treatment of rheumatoid arthritis comprising $^{121}$Tin Hydroxide with a carrier of metal hydroxide aggregate.

31. The radioactive composition of claim 30 wherein the metal hydroxide aggregate is selected from the group consisting of ferric hydroxide and aluminum hydroxide.

32. The composition of claim 30, wherein the metal hydroxide aggregate is a transition metal hydroxide selected from the group consisting of Bismuth Hydroxide, Chromium Hydroxide, Cupric Hydroxide and Manganese Hydroxide.

33. A radioactive composition for the treatment of arthritis comprising $^{121}$Tin in a carrier of a metal hydroxide aggregate having a particle size of approximately from 1 micron-90 microns, Beta energy emissions of said $^{121}$Tin substantially 0.38 MeV, and a half-life of approximately 27.06 hours.

34. A method for the treatment of arthritis of an articular joint comprising: administering by injection a therapeutically effective quantity of a composition which includes $^{121}$Tin and an aggregated metal hydroxide to perform radiation synovectomy.

35. The method of claim 34 wherein the metal hydroxide is selected from the group consisting of ferric hydroxide and aluminum hydroxide.

36. A method for the treatment of arthritis of an articular joint comprising: administering by injection a therapeutically effective quantity of a composition including 121Tin to perform radiation synovectomy.

37. A method for the treatment of rheumatoid arthritis of an articular joint comprising: administering by injection a therapeutically effective quantity of a composition including 121Tin to perform radiation synovectomy.

* * * * *